United States Patent
Khorsandian et al.

[11] Patent Number: 5,146,913
[45] Date of Patent: Sep. 15, 1992

[54] HOLDER AND LOCK FOR ORO-INTUBATION

[76] Inventors: Asphendiar Khorsandian, 337 N. Clyde Morris Blvd., Daytona Beach, Fla. 32114; Jenabe E. Caldwell, 18 Domicilio Ave., Ormand Beach, Fla. 32174

[21] Appl. No.: 663,608

[22] Filed: Mar. 4, 1991

[51] Int. Cl.⁵ .................. A61M 16/00; A61M 5/00; A61M 5/178; A62B 9/06
[52] U.S. Cl. .................. 128/200.26; 128/912; 128/DIG. 26; 128/207.14; 128/207.17; 604/117; 604/165
[58] Field of Search ........ 128/207.14, 207.17, 128/207.18, 205.25, 203.29, 911, 912, DIG. 26, 200.26, 201.26; 604/117, 158, 160, 164, 165, 264

[56] References Cited

U.S. PATENT DOCUMENTS

| | | | |
|---|---|---|---|
| 146,730 | 1/1874 | Vickers | 128/207.14 |
| 316,636 | 4/1885 | Miles | 128/207.14 |
| 900,343 | 10/1908 | Barnes | 128/207.14 |
| 1,266,856 | 5/1918 | Ramsay | 128/207.14 |
| 2,693,182 | 11/1954 | Phillips | 128/207.14 |
| 2,857,911 | 10/1958 | Bennett | 128/207.17 |
| 3,169,529 | 2/1965 | Koenig | 128/207.14 |
| 3,912,795 | 10/1975 | Jackson | 128/207.14 |
| 4,050,466 | 9/1977 | Koerbacher | 128/207.14 |
| 4,270,529 | 6/1981 | Muto | 128/207.17 |
| 4,275,724 | 6/1981 | Behrstock | 128/207.17 |
| 4,326,515 | 4/1982 | Shaffer et al. | 128/207.17 |
| 4,340,046 | 7/1982 | Cox | 128/207.17 |
| 4,471,776 | 9/1984 | Cox | 128/207.17 |
| 4,520,809 | 6/1985 | de Greef | 128/207.18 |
| 4,821,736 | 4/1989 | Watson | 128/207.17 |
| 4,896,666 | 1/1990 | Hinkle | 128/203.29 |
| 4,944,313 | 7/1990 | Katz et al. | 128/207.14 |
| 4,966,141 | 10/1990 | Bacaner et al. | 128/207.14 |
| 5,009,227 | 4/1991 | Nieuwstad | 128/207.17 |

FOREIGN PATENT DOCUMENTS 1437033 11/1988 U.S.S.R. .......... 128/205.25

Primary Examiner—Edgar S. Burr
Assistant Examiner—Kimberly L. Asher
Attorney, Agent, or Firm—Shoemaker & Mattare, Ltd.

[57] ABSTRACT

An orotracheal tube pacifier is disclosed. The orotracheal tube pacifier includes an orotracheal tube, a pacifier portion for receiving the orotracheal tube, fastener means for holding securely the pacifier portion around the patient's head without the need for taping and the ultimate bruising, a face plate to which the fastener means and the pacifier portion are securely attached to, the face plate being relatively large as a safety precaution to hold the pacifier portion, a collet locking device fitting on the face plate and will not slipping or coming loose, and nipples affixed to the face plate and being designed to reduce the amount of palatal grooving.

9 Claims, 2 Drawing Sheets

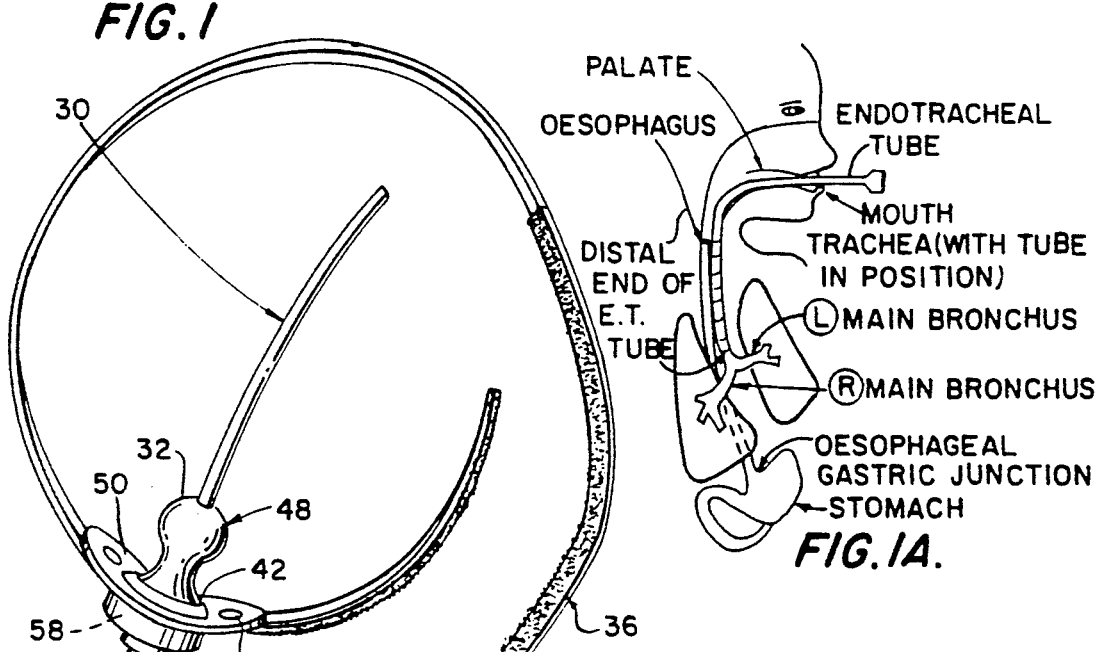
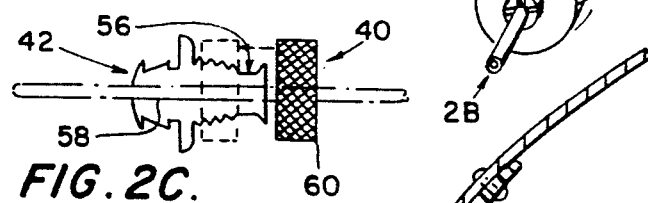
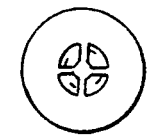
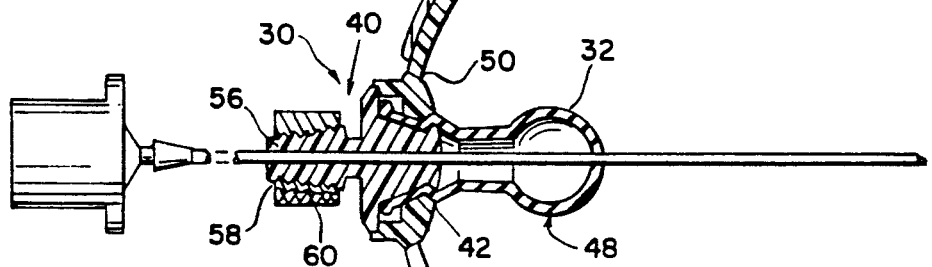
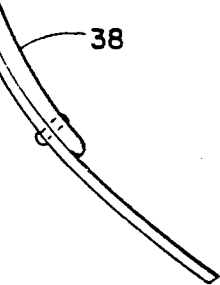

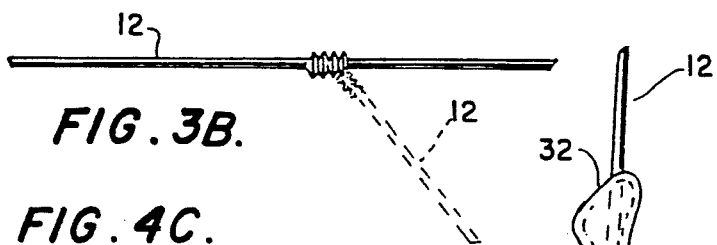
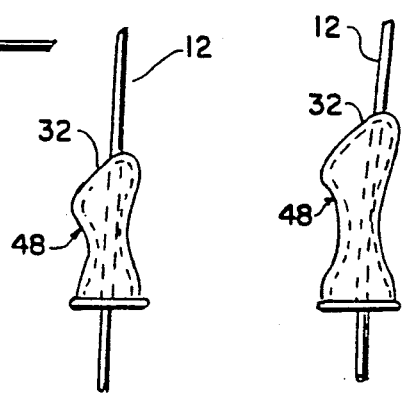
FIG. 3B.
FIG. 6.
"PREME"
FIG. 7.
FULL TERM OR OLDER
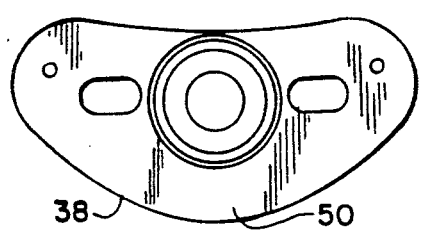
FIG. 4C.
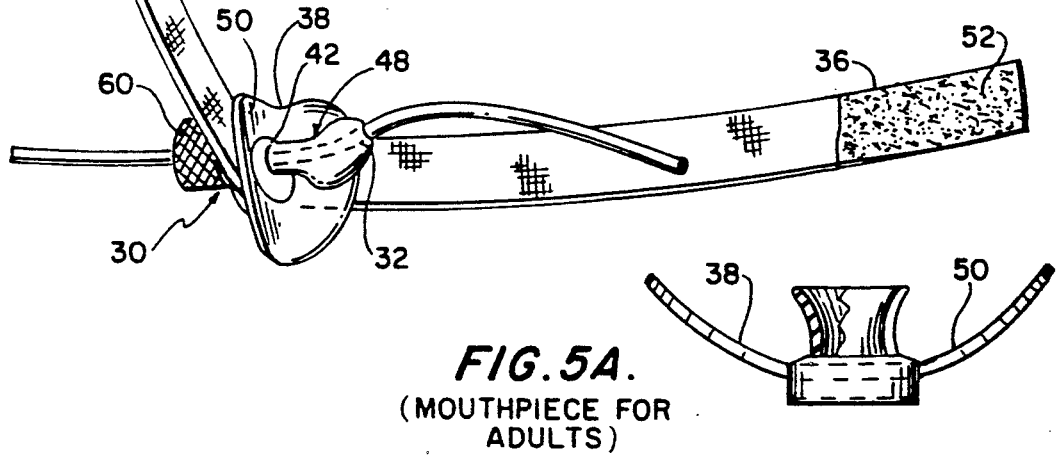
FIG. 4A.
FIG. 4B.
FIG. 5A.
(MOUTHPIECE FOR ADULTS)
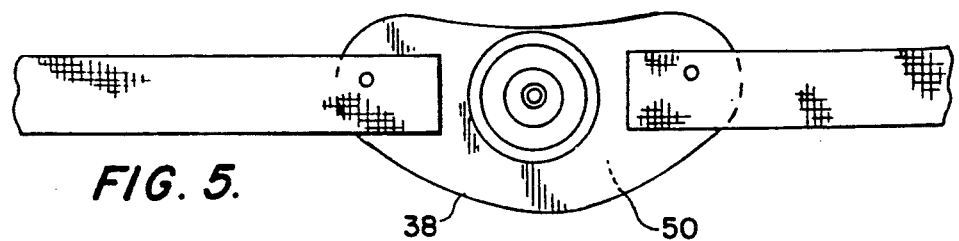
FIG. 5.

HOLDER AND LOCK FOR ORO-INTUBATION

BACKGROUND OF THE INVENTION

1. Field of the Invention

The present invention relates to tracheal and gastro tubes inserted into the lungs or stomaches of patients.

More particularly, the present invention relates to tracheal and gastro pacifiers for use with tracheal and gastro tubes inserted into the lungs or stomaches of infants.

2. Description of the Prior Art

According to S. P. Ash, and J. P. Moss, at the department of Orthodontics, University College Dental School, in a paper published in the British Journal of Orthodontics, Vol. 14/1987, "Prolonged orotracheal intubation was shown to be associated with narrowing, deepening and some anterior elongation of the developing palate." Thirty babies were used in this test of less than 32 weeks of gestation. They further stated, "However, it has been suggested that various dental anomalies may be the result of prolonged endotracheal intubation."

Grahnen et al. (1974) suggested that the prevalence of enamel hypoplasia might be associated with respiratory distress at birth. Saunders et al. (1976) reported two cases of palatal groove formation and Duke et al. (1976) reported two cases of acquired clefts of the hard palate. More recently, Erenberg and Novac (1984), in a retrospective cross-sectional study, found a 47.6 percent incidence of palatal grooving in a group of pre-term infants subject to intubation. Even the use of 'soft' endotracheal tubes does not lead to a reduction in the amount of palatal grooving (Molteni and Brumstead, 1986).

They went on to say, "It is common to find the babies sucking on the tube and this could result in a molding of the oral tissues and in particular the alveolus." They indicated that the evidence shows damage to the tooth buds.

"During reintubation, infants can suffer hypoxemia, bradycardia, and damage to the vocal cords (Thibeault, 1986)." "Death has occurred in some instances (Striker, Stool, and Downs, 1967) (Freeman, 1972)."

An article in Pediatric Radiology (1981) 10: 178-179 by A Delbert Bowen, M. D. reported on 18 cases of swallowed neonatal endotracheal tubes and one additional case of a 36 week gestation infant that swallowed the tube. Dr. Bowen mentioned in the article that fitting the tube with a collar or restraining device would be a precaution.

G. Ginoza, S. Cortez, and H. D. Modanlou, stated, "Possible consequences of the acquired groove include problems with dentition, speech, hearing, and middle ear disease." They further determined from their study that 87.5% of infants that were intubated for 15 days had palatial grooving.

R. A. Molteni and D. H. Bumstead, mentioned local trauma to the upper airways after prolonged intubation and included perforation, vocal cord edema, granuloma formation, subglottie cysts, unilateral or bilateral cord paralyaia, subglottic stenosis, and tracheitis.

A. Erenberg reported that the incidence of palatial groove was greatest in the neonate using the tube for 15 days or longer but was noted in one infant after only 12 hours of use.

An article by G. M. Angelos, D. R. Smith, R. Jorgenson, and E. A. Sweeney confirms the problem of future dental problems when using neonatal oral tracheal intubation. Also, another observation was made in this article that Sullivan (1982) describes that infants born after 26-36 weeks' gestation had neither sucking nor a coordinated swallowing reflex and had to be fed by sasogastric tubes. He suggested using orotracheal tubes for feeding if the tubes can be held securely.

According to R. C. Witzel, he stated, "while requiring oral endotracheal intubation, develop erosions of the upper alveolar ridge in precisely the position suggested by the report." He further stated, "I suggest, therefore that the lesion occurs as a result of drag on the endotracheal tube in this alveolar slot, which gives rise to pressure necrosis of the alveolar ridge and underlying tooth but. This acute lesion and its long-term sequelae could be prevented by avoiding contact with the alveolar ridges.

The adults and children beyond the pacifier stage are known to bite on the tracheal and gastro tubes, thus obstructing their functional use. Also, it is common to have accidental extubation with tape failure.

Numerous innovations for tracheal and gastro tubes have been provided in the prior art that are adapted to be used. Even though these innovations may be suitable for the specific individual purposes to which they address, they would not be suitable for the purposes of the present invention as heretofore described.

SUMMARY OF THE INVENTION

Accordingly, it is an object of the present invention to provide an orotracheal tube pacifier and holder that avoids the disadvantages and complications of the prior art.

More particularly, it is an object of the present invention to provide a secure lock on the tube. It was noted that the babies, especially the premature infants, would try to chew on the tube and thus cause later problems in gums, teeth, palates, and even some more severe complications. It is natural for a baby to suck, which calms the child. Also it induces the production and secretion of digestive enzymes.

It was further noted that using the adhesive tape caused the child to be bruised when it was removed and caused unnecessary pain, and produced secondary complications at the site of the tape.

A prototype orotracheal tube pacifier and holder was made. The tracheal tube passed through the center of the pacifier and holder and was clamped in place at the proper depth and held secured with the collet, and is secured around the babies' head with VELCRO®. Once a patent is secured, further testing and more advanced tube pacifiers and holders will be tested and modified in preparation for marketing.

In keeping with these objectives, and with others which will become apparent hereinafter, one feature of the present invention resides, briefly stated, in an orotracheal tube pacifier and holder, comprising an orotracheal tube, a pacifier portion for receiving the orotracheal tube, fastener means for holding securely the pacifier portion around the patient's head without the need for taping and the ultimate bruising, a face plate to which the fastener means and the pacifier portion are securely attached to, the face plate being relatively, large as a safety precaution to hold the pacifier in position, a collet locking device fitting on the face plate so that it will not slip or come loose, and the pacifier is affixed to the face plate being designed to reduce the amount of alveolar and palatal grooving.

In accordance with another feature of the present invention, the fastening means include VELCRO ®.

Another feature of the present invention is that the orotracheal tube contains a bellows portion where the orotracheal tube can bend 90° without collapsing. The orotracheal tube is kept away from the palatal ridge of the patient by the bellows an pacifier. The patient can still suck, keep the tube in the mouth in the proper position, and also thus sooth the patient and help the patient develop proper sucking and coordinated swallowing reflexes.

Yet another feature of the present invention is that the nipples are designed with the top curved and rounded to fit the pallet of the patient in order to protect the patient from the grooving caused by a tracheal tube alone, the bottom of the nipple is only slightly rounded for the patient's tongue.

Still another feature of the present invention is that the nipples are one homogeneous piece, simple walled, and made from a hollow body of elastomeric material.

Yet still another feature of the present invention is that the face plate has an inner surface and is curved to fit the patient's face, the nipple reaches and is connected to the inner surface of the face plate of the patient. The face plate has two (2) holes for ventilation and the insertion of other needed oral devices.

Still yet another feature of the present invention is that the faceplate is held securely in place, with VELCRO ®, around the patient's head.

Another feature of the present invention is that it further comprises a plug end. The plug securely fastens the nipple to the face plate and locks into the face plate.

Yet another feature of the present invention is that the collet has a collet center hole.

Still another feature of the present invention is that the collet center hole is sized for the tracheal tube and is split to lock the tracheal tube in place without closing off the tracheal tube if the collet is over tightened.

The novel features which are considered characteristic for the invention are set forth in particular in the appended claims. The invention itself, however, both as to its construction and its method of operation, together with additional objects and advantages thereof, will be best understood from the following description of the specific embodiments when read in connection with the accompanying drawing.

BRIEF DESCRIPTION OF THE DRAWING

FIG. 1 is a perspective view of the tube pacifier of the present invention;

FIG. 1A is perspective view of the tube pacifier of the present invention, shown applied to a phantom head;

FIG. 2A is a perspective view of the securing device of the tube holder of the present invention;

FIG. 2B is a plan view of the tube pacifier of the present invention taken in the direction of the arrow 2B of FIG. 2A;

FIG. 2C is cross-sectional view of the collet and the plug of the present invention with the collet nut being tightened around the tube to lock the tube in place, the left end being the "plug end" which will hold the pacifier, also the plug locks the collet onto the face plate;

FIG. 3A is a top view in partial cross-section of the tube pacifier of the present invention;

FIG. 3B is a side view of the tube with the integral bellows;

FIG. 4A is perspective view of the tube pacifier of the present invention;

FIG. 4B is a side view of the face plate;

FIG. 4C is top view of the face plate;

FIG. 5 is a top view of the face plate with the straps attached;

FIG. 5A is a side view in partial cross-section of a face plate for an adult;

FIG. 6 is a side view of the tube passing through a nipple for a premature baby; and FIG. 7 is a side view of the tube passing through a nipple for a full term or older baby.

DETAILED DESCRIPTION OF THE PREFERRED EMBODIMENT

It has been noted that infants 10 that are in need of an orotracheal intubation 12 that must pass through the babies mouth 14 for the lungs 16 or for the stomach 18 often develop a distorted mouth 20, pallet 22, gums 24, and later on even the teeth 26. It has also been noted that by taping the tracheal tube in place with tape 28 across the child's face, it is not only painful in removal but often leaves a bruise and secondary complications on the face that is distressful to the parents. Taping and not locking the tube holder has been the cause of swallowing neonatal endotracheal tubes 12, extubation, and kinking of the tube.

The present invention is an orotracheal tube pacifier 30 and holder, where the tube 12 is passed through a holder locking device and a pacifier 32 and is held securely around the patient's head 34 with a VELCRO ® strap fastener 36, that does away with the taping 28. The VELCRO ® strap 36 is securely attached to the restraining face plate 38. The face plate 38 is quite large as a safety precaution to hold the tracheal tube pacifier 30.

The face plate 38 is fitted with a collet locking device holder 40 that when tightened will not slip or come loose. The orotracheal tube pacifier nipple 48 has been designed to reduce the amount of palatal grooving (not shown) and help solve the other problems now faced by the use of orotracheal intubation.

The tube 12 itself has also been redesigned in order to make a 90° turn without collapsing the tube 12 from the pallat 22 ridge. This will allow the baby 10 to suck, keep the tube 12 in the proper position in the patient's mouth 14, and also sooth the child 10. Also, helping the child 10 develop proper sucking and coordinated swallowing reflexes (not shown), which also enhances the gastric secretions which helps in digestion. Because the orotracheal pacifier tube 12 is held securely, it can be used for feeding the patient 10, and also the tracheal tube pacifier 30 and holder can be used to insert and hold an orogastric tube.

The nipples 48 are designed with the top curved and rounded to fit the pallet 22 of the patient 10 in order to protect the child's 10 palate 22 and gums 24 from grooving (not shown) caused by a tracheal tube 12 alone. The bottom of the nipple 48 is only slightly rounded for the babies 10 tongue. All the nipples 48 are one piece, single walled, and are made from a hollow body of elastomeric material.

The face plate 38 is curved to fit the patient's 10 face, by having an inner surface 50, where the nipple 48 is connected to the face plate 38, and extends to the inner surface 50 of the face plate 38. This face plate 38 is then held securely in place with VELCRO ® 36 around the patient's head 34. This face plate 38 can be used for any and all patients 10 that require oral intubation. For older children and adults only the pacifier 32 is omitted.

A plug 42 securely fastens the nipple 48 to the face plate 38 at one end, with a tapered collet 56 on the other end. The collet center hole 58 is sized for the tracheal tube and split to lock the tracheal tube 12 without closing off the tube 12 if the collet 56 is over tightened.

The threaded collet nut 60 threads onto the split collet 56 and tightens down on, and locks the tube 12, securely in place. Yet by a simple twist, the whole device ca be removed leaving only the orogastric or orotracheal tube 12 in place and undisturbed.

The new design of the endotracheal tube 12 with the bellows type construction, will allow for insertion at almost 90° without crimping or in any way impeding the material flow to the patient 10.

The tube 12 will be inserted into the patient 10 and set at the proper depth. The tube 12 would then be turned at the back of the throat until it is totally clear of the upper alveolar ridge. The bellows being used provide adjust for the proper angle. Then the orotracheal device 12 will be threaded onto the tube 12 and the device 12 firmly locked with the collet 56 and the face plate 38 fastened around the patients head 34 with the VELCRO ® fastener 36.

The tube 12 may be connected to a gavage feeder, ventilator, or any other device requiring oral intubation of a patient.

It should be understood that FIG. 5A is a mouthpiece that is an integral part of the face plate 38. A soft elatomer sleeve is disposed over the plastic for the older patient's teeth 26 so that the tube 12 is protected from chewing by the patient 10. The collet 56 and plug 42 holder are then locked into the face tube 12 at the proper depth in the patient 10. The face plate 38 is secured by VELCRO ®.

It will be understood that each of the elements described above, or two or more together, may also find a useful application in other types of constructions differing from the type described above.

While the invention has been illustrated and described as embodied in an orotracheal tube and holder, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is desired to be protected by Letters Patent is set forth in the appended claims.

I claim:

1. A device for oral intubation, comprising
a face plate having a thickened central portion with a central aperture therethrough and a large peripheral flange to prevent the device from being swallowed, said flange being shaped to contact a patient's face beneath the nose,
a hollow, resilient bite protector having an open proximal end inserted in said aperture, and a distal end having a through hole,
a lock member comprising a core having a plug protruding into the end of the bite protector, the plug extending through the central face plate aperture, and into the distal end of the bite protector, for locking both the bite protector and the lock member to the face plate,
said lock member further having a peripheral flange abutting a front surface of the face plate, and an externally tapered and threaded collet portion split by longitudinal cuts into plural segments, each capable of limited movement in a radial direction, and an internally tapered and threaded nut engaged with the threads on the collet portion, and
an orotracheal tube extending entirely through said lock member, said face plate, and said bite protector through-hole, whereby the tube is prevented from contacting the upper palates and said tube can be secured without damage in the lock member by tightening said nut, thus forcing the collet segments inward against the tube.

2. The invention of claim 1, wherein said thickened central portion has a counterbore on its front face, for receiving the open proximal end of said bite protector, and for seating the peripheral flange of said lock member.

3. The invention of claim 1, wherein said orotracheal tube has a distal portion extending past the hole in the bite protector into the mouth of a patient, and only part of said distal portion is provided with a flexible bellows portion that allows the tube to bend easily at the back of the throat without crimping, to prevent bending of that portion within the mouth so as to avoid damage to the upper palates of the patient.

4. The invention of claim 1, further comprising a pair of retaining straps affixed to opposite sides of the face plate, said straps being of sufficient length to pass around the head of the patient, and having quick-release fasteners thereon providing for continuous length adjustment for different sized patients.

5. The invention of claim 1, wherein the face plate has a pair of side holes, one on either side of the central aperture, each adapted to receive an auxiliary tube for feeding, medication or the like.

6. The invention of claim 1, further comprising means for retaining the nut on the collet, so that the nut cannot be lost.

7. The invention of claim 1, wherein the bite protector is a pacifier having a rounded end in which said through hole is formed, a round top surface for protecting the hard palate, and a round bottom surface for engaging the tongue.

8. The invention of claim 1, wherein the lock member holds the orotracheal tube and the bite protector on a common axis to prevent the tube from being bitten by the patient.

9. The invention of claim 1, wherein the plug of the lock protector has a peripheral lip, providing a snap fit into the face plate aperture.

* * * * *